US011752033B2

(12) United States Patent
Howat

(10) Patent No.: US 11,752,033 B2
(45) Date of Patent: Sep. 12, 2023

(54) ITEM OF HEADWEAR FOR COOLING THE HEAD

(71) Applicant: Jonathan Howat, Headington (GB)

(72) Inventor: Jonathan Howat, Headington (GB)

( * ) Notice: Subject to any disclaimer, the term of this patent is extended or adjusted under 35 U.S.C. 154(b) by 661 days.

(21) Appl. No.: 15/728,996

(22) Filed: Oct. 10, 2017

(65) Prior Publication Data
US 2018/0098880 A1 Apr. 12, 2018

(30) Foreign Application Priority Data
Oct. 10, 2016 (GB) ..................................... 1617149

(51) Int. Cl.
*A61F 7/02* (2006.01)
*A61F 7/10* (2006.01)
*A42B 1/008* (2021.01)
*A61F 7/00* (2006.01)

(52) U.S. Cl.
CPC ................ *A61F 7/10* (2013.01); *A42B 1/008* (2013.01); *A61F 7/02* (2013.01); *A61F 2007/0002* (2013.01); *A61F 2007/0007* (2013.01); *A61F 2007/0008* (2013.01); *A61F 2007/0011* (2013.01); *A61F 2007/0233* (2013.01); *A61F 2007/0268* (2013.01)

(58) Field of Classification Search
CPC ...... A61F 7/10; A61F 7/02; A61F 2007/0011; A61F 2007/0008; A61F 2007/0007; A61F 2007/0002; A61F 2007/0233; A61F 2007/0268; A61F 2007/0225; A61F 2013/00919; A61F 2013/00187; A61F 2007/0009; A42B 1/008
See application file for complete search history.

(56) References Cited

U.S. PATENT DOCUMENTS

| | | | | | |
|---|---|---|---|---|---|
| 1,569,877 | A | * | 1/1926 | Owens | A61F 7/08 607/112 |
| 4,552,149 | A | * | 11/1985 | Tatsuki | A61F 7/10 607/110 |
| 5,163,425 | A | * | 11/1992 | Nambu | A42B 1/008 607/110 |
| 5,957,964 | A | * | 9/1999 | Ceravolo | A61F 7/10 607/109 |
| 2003/0055473 | A1 | * | 3/2003 | Ramsden | A61F 7/10 607/109 |

(Continued)

FOREIGN PATENT DOCUMENTS

| | | |
|---|---|---|
| DE | 3210178 | 9/1983 |
| WO | WO9606580 | 3/1996 |
| WO | WO2015120388 | 8/2015 |

OTHER PUBLICATIONS

United Kingdom Intellectual Property Office, Examination Report for Application GB1617149.8, dated Feb. 28, 2017.

(Continued)

*Primary Examiner* — Kaitlyn E Smith
*Assistant Examiner* — Yasamin Ekrami
(74) *Attorney, Agent, or Firm* — Chad Hinrichs, PLLC

(57) ABSTRACT

Headwear for cooling the neurocranium region of a user's head and thereby the user's brain. In particular, the headwear provides selective cooling to specific areas of the parietal region, the frontal region, the temporal region and the occipital region of the cranium associated with the drainage system of the brain following a traumatic injury.

19 Claims, 5 Drawing Sheets

(56) References Cited

U.S. PATENT DOCUMENTS

2014/0046410 A1    2/2014  Wyatt
2014/0379058 A1*  12/2014  Farrago ................. A61F 7/02
                                                      607/110
2016/0354232 A1*  12/2016  Rozental ................ A61F 7/10

OTHER PUBLICATIONS

Applicant's Response to Combined Search and Examination Report, dated May 11, 2017.
Examiner's Response, dated May 18, 2017.

* cited by examiner

ITEM OF HEADWEAR FOR COOLING THE HEAD

1. PRIORITY CLAIM

The present application claims priority to United Kingdom Patent Application Number GB1617149.8 filed on Oct. 10, 2016.

2. FIELD OF THE INVENTION

The present invention relates to headwear for cooling the neurocranium region of a user's head and thereby the user's brain. In particular, the headwear provides selective cooling to specific areas of the parietal region, the frontal region, the temporal region and the occipital region of the cranium associated with the drainage system of the brain following a traumatic injury.

3. BACKGROUND OF THE INVENTION

It is known to provide cooling to areas of the body that have suffered from violent trauma, particularly during contact sports, such as rugby union, boxing, equine sports, or cycling for example. Typically, this cooling is provided pitch-side before further treatment can be provided if necessary. This is achieved by the use of packs, which comprise frozen liquid or chemicals selected to produce endothermic reactions. Prior art first-aid brain cooling devices comprise helmets with cooling material spread substantially evenly across the entirety of the neurocranium, encompassing the entirety of the parietal region and the majority of the frontal and occipital regions. These devices are focussed on cooling the brain as a whole, and do not concentrate that cooling specifically on the drainage system. As a result, the regions of the brain covered by prior art devices do not extend over the full area of the skull that corresponds with the drainage system.

4. SUMMARY OF THE INVENTION

The inventor has identified that preventing a build-up of blood and cerebro-spinal fluid in the brain helps to prevent further damage to the brain. When the brain swells, fluid cannot leave the brain to balance the fluid going into the brain. This occurs as tissue becomes engorged and compresses vessels. This compression restricts the drainage of the brain and hence increases intra-cranial pressure.

Cooling of the drainage system can reduce the resistance to fluid leaving the brain, thereby allowing the pressure to equalise naturally. The drainage system extends as far forward as the *glabella* (brow line) and as far back as the $5^{th}$ and $6^{th}$ cervical vertebrae (the lower neck). Importantly, there is a confluence of the sinuses at the internal occipital protuberance, and further drainage vessels at the occipital/C1, C1/C2, C2/C3, and C3/C4 junctions.

The inventor has established that advantageous effects can be achieved by cooling that is targeted to the circulatory system of the brain and, in particular, the drainage of the circulatory system. Without wishing to be bound by theory, it is believed that the selective cooling can set up temperature gradients to direct the flow of heat and thereby more effectively reduce, or prevent the increase of, intra-cranial pressure.

Accordingly, there is provided headwear as defined by claim 1.

Additionally, there is provided headwear as defined by claims 25 and 27.

5. BRIEF DESCRIPTION OF THE DRAWINGS

For a better understanding of the invention and to show how the invention may be put into effect, reference is now made, by way of example only, to the accompanying drawings in which.

Figure 3:
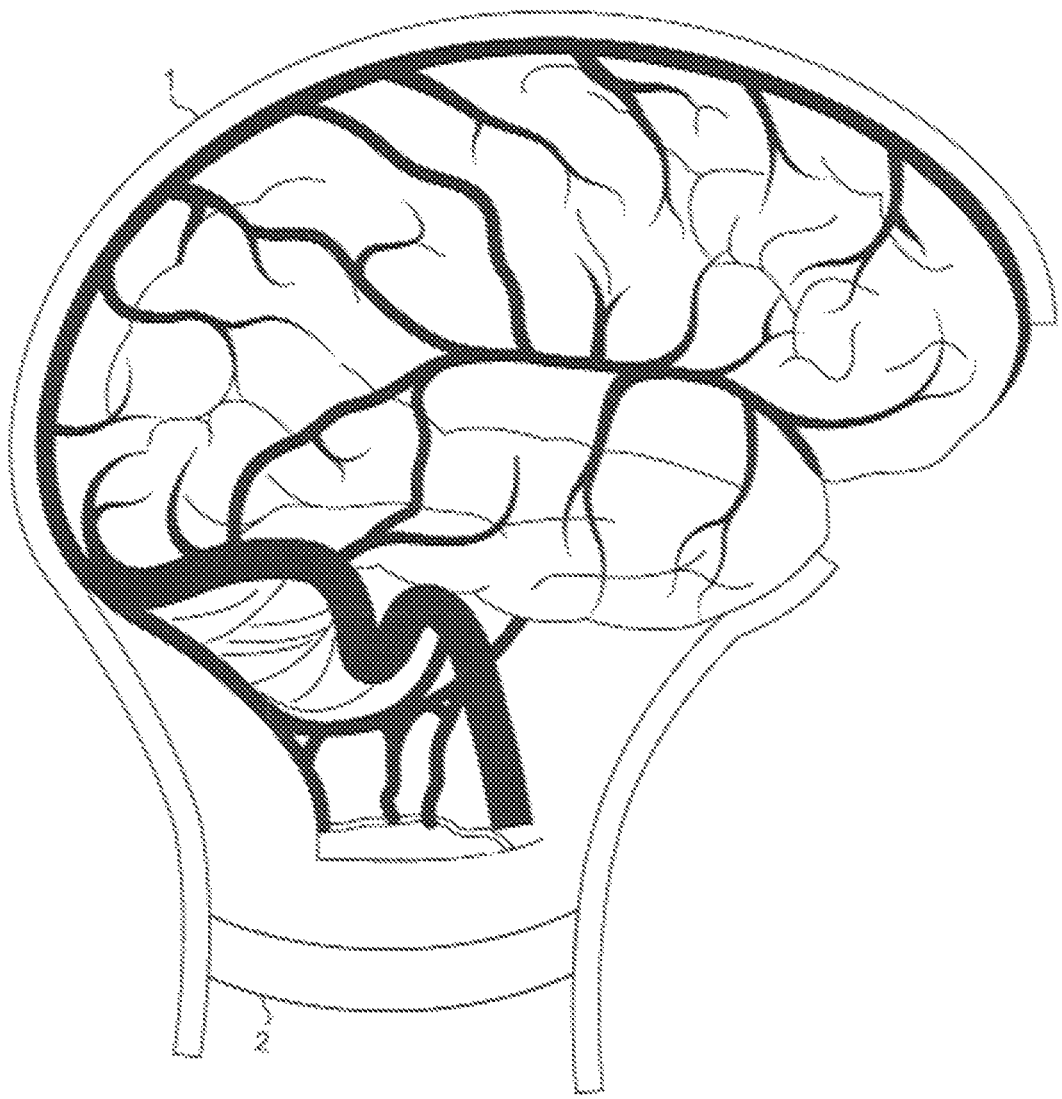
FIG. 3 shows a side sectional view of the headwear of FIG. 1.
Figure 4:
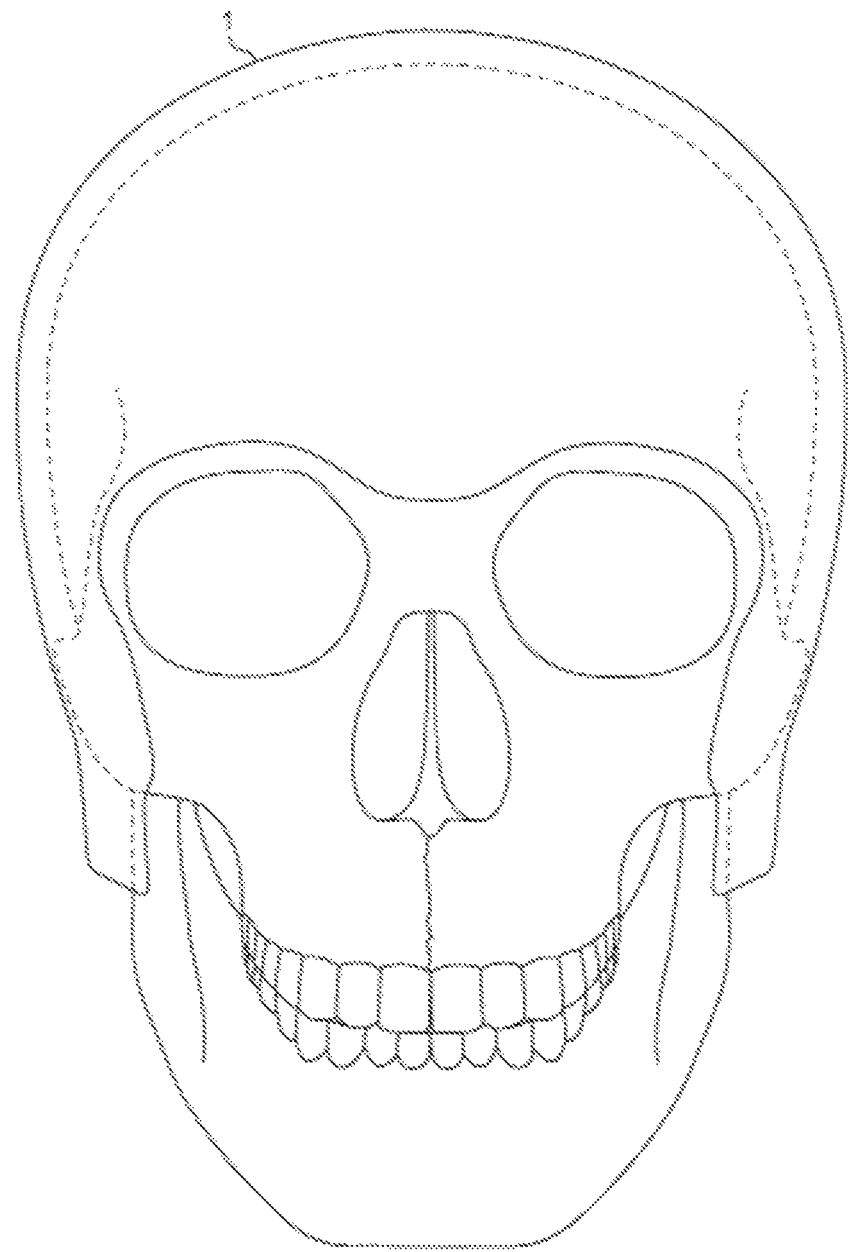
FIG. 4 shows a front view of the headwear of FIG. 1 relative to a user's cranium.

For convenience, the user's skin has been omitted in FIGS. 3 and 4. The user's skull has also been omitted in FIG. 4.

6. DETAILED DESCRIPTION OF THE INVENTION

Figure 1:
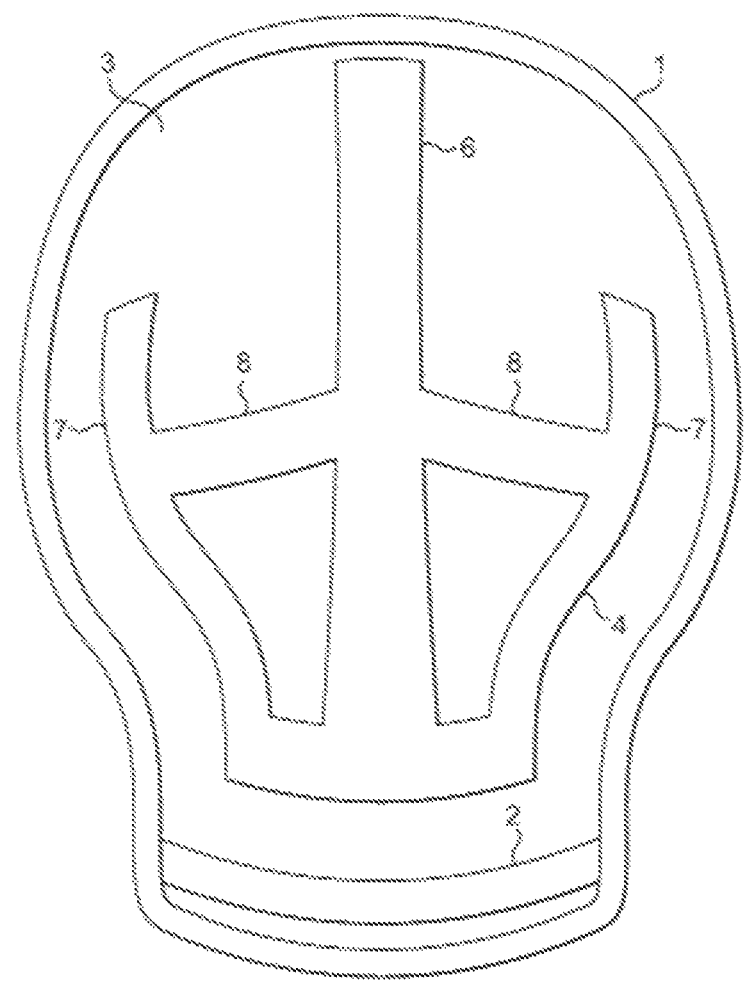
FIG. 1 shows a sectional view of headwear according to an embodiment of the present invention.
Figure 5:
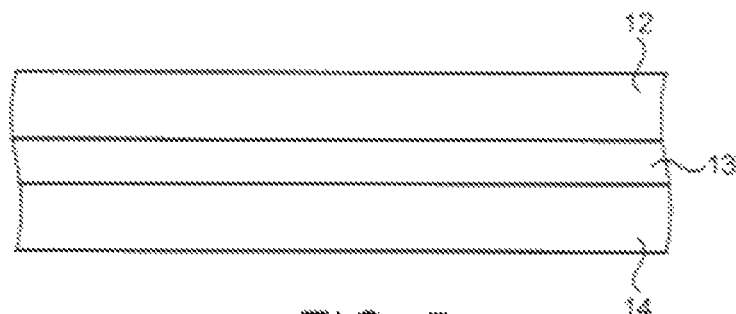
FIG. 5 shows a cross sectional view of the headwear of FIG. 1.

FIG. 1 depicts an item of headwear in accordance with the invention. As shown in FIG. 5, the headwear 1 is comprises three major layers 12, 13, 14. Two of the layers are support layers 12, 14, and the third is a cooling layer 13. The cooling layer 13 is sandwiched between the first and second support layers 12, 14.

Figure 2:
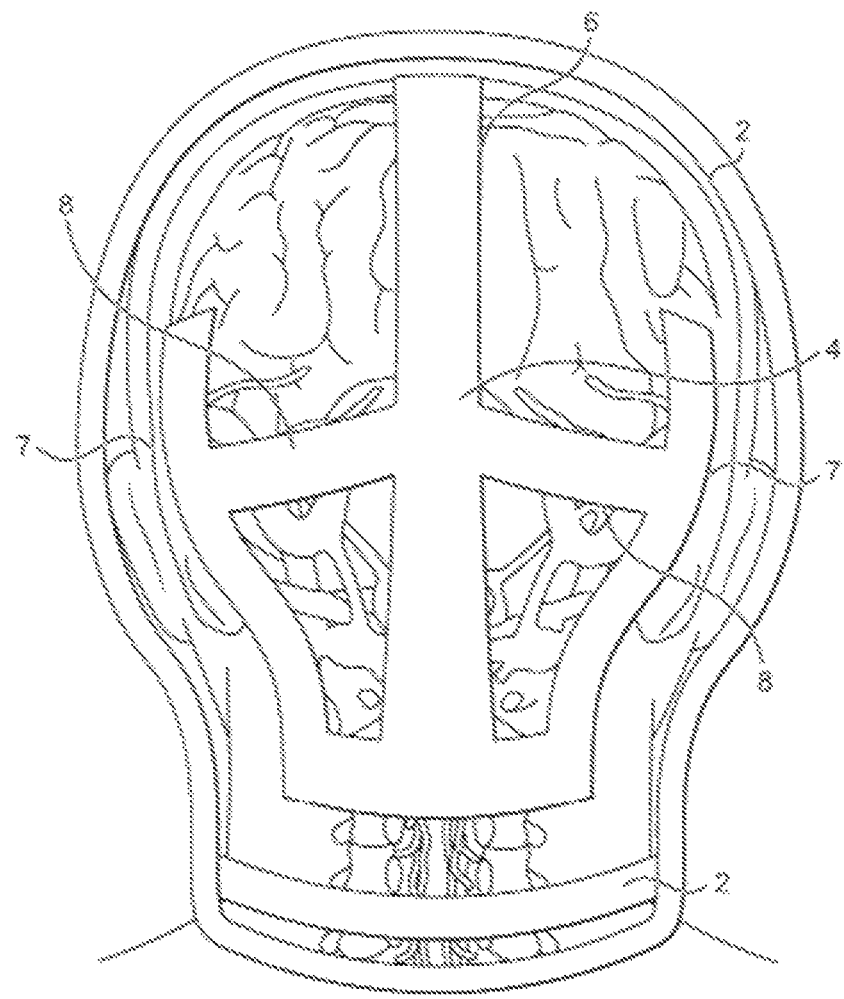
FIG. 2 shows the sectional view of FIG. 1 as worn by a user.

In use, as depicted in FIGS. 2 and 3, the headwear 1 extends over a substantial part of the user's cranium. Preferably, the cooling layer 13 extends over the frontal bone until just above the ocular arches. The cooling layer 13 preferably extends to cover the malar(zygomatic)/frontal junction, the greater wings of the sphenoid, the temporal squamae and both temporo mandibular joints. This protects the trigeminal ganglia. The cooling layer 13 extends over the ears of the user and the angle of the mandible.

The cooling layer 13 covers (but, as explained below, does not necessarily cool) all of the parietal bone and extends past the lambda and bregma landmarks. Preferably, the cooling layer 13 covers (but does not necessarily cool) all of the parietal, frontal and occipital bones.

The front of the cooling layer 13 preferably extends as far forward as the glabella (brow line) in order to cover the full frontal extent of the superior saggital sinus.

The back of the cooling layer 13 preferably extends towards the clavicle, covering the base of the occiput. Preferably, the back of the cooling layer 13 covers the base of the occiput. More preferably, the back of the cooling layer 13 covers the atlanto-occipital membrane. Even more preferably, the back of the cooling layer 13 covers the vertebral venous plexus between the mastoids.

A bottom portion of the cooling layer 13 extends down over the cervical spine to the $4^{th}$ cervical vertebrae in order to cover the confluence of drainage vessels. More preferably, the bottom portion of the cooling layer 13 extends down over the cervical spine past the $6^{th}$ cervical vertebrae. The base of the headwear 1 is located at the vertebral prominence of the 7th cervical/1st thoracic junction.

The headwear 1 thus forms a neurocranial portion and a neck portion. The neurocranial portion is substantially dome-shaped, with a central cavity for receiving the wearer's skull. An opening is provided in a front portion that corresponds substantially to the wearer's facial skeleton. Preferably, the opening has two curved arches at the front edge of the headwear 1 for the wearer's eye region.

The headwear 1 encapsulates the entire neurocranium and the two lateral aspects and the posterior aspect of the cervical spine. The headwear 1 is provided with an attachment portion in the neck (cervical) area, preferably near the $5^{th}$ or $6^{th}$ cervical vertebrae. Preferably, the attachment portion comprises a band 2 of material extending in a segment of a circle, which may extend, for example, up to 270° around the rear of the neck. The band 2 preferably has a frontal opening for the user's neck for putting the headwear 1 on.

The band 2 may be pre-stressed with a bias to return to its original shape. In this manner, the band 2 secures the headwear 1 to the user. The band 2 may be formed in different sizes, such that different headwear may better fit different users. As the swelling subsides, the band 2 resizes with the user's neck. The headwear 1 may further comprise an additional means to secure the headwear in place. This may take the form of clips, Velcro or other similar attachments. For example, a chin strap or the like.

The first layer 14 of the headwear 1 contacts with the user's head and covers the regions identified above. The third layer 12 of the headwear 1 is substantially the same shape as the first layer 14. In preferred embodiments it is manufactured from the same material as the first layer 14.

The third layer 12 may be formed of, or comprise, one or more of: neoprene, silicone, and/or polyurethane.

The second layer 13 of the headwear 1 comprises the cooling structure 3 of the headwear 1. The structure 3 comprises a network of interconnected cooling portions, preferably formed as vessels 4 which are filled with a cooling agent. The network 4 is configured to provide selective cooling of the wearer's head and so does not extend completely through the second layer 13. That is, certain locations of the second layer 13 will not hold any cooling agent. For example, the headwear 1 may completely cover the wearer's parietal region of the cranium, but structure 3 will not cool the entire surface area of the parietal region.

While the present embodiment is described with first and second support layers 12, 14 and a cooling layer 13, the headwear 1 may be formed of any number of layers. In particular, the headwear 1 could comprise a cooling layer formed of first and second outer layers, with a network of interconnected vessels 4 therebetween. However, it is preferred to provide additional layers for comfort and structured strength.

The cooling agent may be any suitable chemical, but preferably it will be a fluid, and preferably will not lose motility when exposed to low temperatures. The cooling agent may comprise, for example, BlueIce®, aqueous glycerol, and/or saline solution (for example, of around 33% salt).

The network of vessels 4 may be formed between two layers of elasticised material to form the cooling layer 13. These layers of material may be joined together, for example, by crimping or by any other fluid-tight means, at various points so as to contain the cooling agent.

In preferred embodiments, the network of vessels 4 of the cooling structure 3 is a closed system. In such embodiments, the cooling structure can be pre-cooled by storing it at a low temperature. Alternatively, the cooling agent may generate an endothermic reaction. Such cooling agents are well known in the field. This allows the headwear to be used pitch-side in sports situations.

The network of vessels 4 comprises one major vessel 6 and two minor vessels 7 extending from the attachment band 2 towards the front edge of the headwear 1. The major vessel 6 and minor vessels 7 may be interlinked with a number of connecting vessels 8. In particular the embodiment depicted in the drawings shows two connecting vessels 8.

This network of vessels 4 is aligned with the brain vessels which form the major drainage areas of the brain. Preferably, this includes the entire surface area of the venous sinus system. The major vessel 6 extends along a centreline of the headwear 1. As shown in FIG. 2, the major vessel 6 is substantially aligned with the superior sagittal sinus of the user in order to provide cooling to this sinus.

The front of the major vessel 6 preferably extends as far forward as the *glabella* (brow line) in order to cover the full frontal extent of the superior sagittal sinus. Preferably, major vessel 6 covers the internal occipital protuberance. More preferably, the major vessel 6 covers the base of the occiput. Even more preferably, the major vessel 6 covers the vertebral venous plexus. The major vessel 6 most preferably extends down over the cervical spine to the 4th cervical vertebrae in order to cover the confluence of drainage vessels, and in some embodiments as far as the 6th cervical vertebrae.

The two minor vessels 7 are substantially aligned with the confluence of the sinuses, transverse sinuses, the sigmoid sinuses, and the internal jugular veins of the of the users, in order to provide cooling to these sinuses. The two minor vessels 7 are arranged to meet the major vessel 6 at a location on the headwear 1 that will—in use—substantially cover the confluence of the underlying sinuses.

The connecting vessels 8 are substantially aligned with the transverse sinuses in order to provide cooling to these sinuses. Preferably, the connecting vessels 8 extend from the major vessel 6 at approximately 40% of its length from the band 2. Preferably, the connecting vessels 8 extend from the major vessel 6 in a substantially perpendicular direction (that is, the tangents of the connecting vessels 8 and the major vessel 6 are perpendicular at their intersection). Preferably, each of the connecting vessels 8 extend from the major vessel 6 to the corresponding minor vessel 7 by a distance of from 70 mm to 90 mm, most preferably 80 mm.

In the embodiment shown in the drawings, the network of vessels is a single continuous system. However, each vessel may be sealed as an independent system and/or each vessel may be formed of multiple independent cooling vessels.

Venous blood and Cerebro-Spinal Fluid (CSF) leaves the brain via these sinuses. In cases of trauma to the brain, the passage through these sinuses may become inhibited. By providing selective cooling to these areas, swelling may be reduced. This results in a reduction of the compression of the vessels, the brain stem, spinal cord and the expansive tissue in the neck. The areas not covered by the cooling vessels are not cooled and hence the side effects associated with complete neurocranial cooling can be avoided This cooling effect allows improved drainage from vital components of the brain, reducing "pressure conus", interstitial edema, cytotoxic waste and possible cerebellar tonsilar ectopia. Additionally, the flow of oxygenated arterial blood back into the brain is increased. This reduces the blood pressure build up and reduces considerably the possible effects of stroke and physiologic shock.

The above description has been given with reference to sinuses that are not themselves part of the item of headwear. However, the description given will be understood by the Skilled Person who knows how to configure the vessels 6, 7, 8 to cover the sinuses when the item of headwear is worn by a user.

In a typical embodiment, the length of the major vessel will be in the range of 430 mm to 480 mm. The connecting vessels will extend over a length in the range of 140 mm to 160 mm. The connecting vessels will extend from a point distanced from the bottom (neck end) of the major vessel in the range of 80 mm to 130 mm. The minor vessels will extend from the connecting vessels toward and away from the neck band of the headwear. In particular, they will extend away from the connecting vessel in the direction away from the neckband by a length in the range of 140 mm to 160 mm.

The vessels 4 are sized to be at least 30% wider than the brain vessels which they are aligned with. Typically the major vessel is between 50 mm and 60 mm wide, the minor vessels are between 50 mm and 60 mm wide, and the connecting vessels are between 50 mm and 60 mm wide. This ensures that the relevant brain vessels are sufficiently covered for cooling by the headwear 1.

What is claimed is:

1. A headwear for cooling a wearer's head, comprising a cooling structure carrying a cooling agent, the cooling structure arranged for cooling the wearer's head and arranged to extend rearwardly past the wearer's internal occipital protuberance when the headwear is worn on the wearer's head, wherein the cooling structure comprises:
   a first cooling portion configured such that when the headwear is worn on a the wearer's head it overlies the superior sagittal sinus, the first cooling portion configured to extend from the $4^{th}$ cervical vertebrae through the rear of the superior sagittal sinus to the front of the superior sagittal sinus, wherein the first cooling portion has a width of between 50 mm and 60 mm and sets up a temperature gradient between the superior sagittal sinus and the area of the wearer's head adjacent the first cooling portion when the headwear is worn on the wearer's head; and
   a plurality of secondary cooling portions that extend from the first cooling portion and are configured such that when the headwear is worn on the wearer's head they overlie the transverse sinuses wherein the plurality of secondary cooling portions each have a width of between 50 mm and 60 mm and set up a temperature gradient between the transverse sinuses and the area of the wearer's head adjacent each secondary cooling portion of the plurality of secondary cooling portions when the headwear is worn on the wearer's head; and
   a plurality of tertiary cooling portions that each extend from a secondary cooling portion of the plurality of secondary cooling portions and are configured such that when the headwear is worn on a wearer's head they overlie the sigmoid sinuses wherein the tertiary cooling portions each have a width of between 50 and 60 mm and set up a temperature gradient between the sigmoid sinuses and an area of the wearer's head adjacent each tertiary cooling portion of the plurality of tertiary cooling portions when the headwear is worn on the wearer's head; and
   gaps that do not provide a cooling effect located between the first cooling portion and the plurality of secondary cooling portions and between each of the secondary cooling portions of the plurality of secondary cooling portions.

2. The headwear according to claim 1, wherein the plurality of secondary cooling portions are arranged to cover only the area of the wearer's head corresponding to the transverse sinuses for cooling thereof.

3. The headwear according to claim 1, wherein the cooling structure does not entirely cover the region of the headwear corresponding to the wearer's parietal region.

4. The headwear according to claim 1, wherein the secondary cooling portions extend from the first cooling portion at a location that when the headwear is worn on the wearer's head they overlie the point at which the superior sagittal sinus meets the transverse sinuses.

5. The headwear according to claim 4, wherein the first cooling portion is arranged to extend along a midline of the headwear forwardly of the wearer's *glabella*.

6. The headwear according to claim 1, wherein the plurality of tertiary cooling portions comprises two tertiary cooling portions symmetrically offset either side of the first cooling portion.

7. The headwear according to claim 1, wherein the first cooling portion has a length of at least 430 mm.

8. The headwear according to claim 1, wherein the secondary cooling portions extend over a length of at least 140 mm.

9. The headwear according to claim 1, wherein the plurality of secondary cooling portions extend from the first cooling portion at a point which is at least 80 mm from an end of the first cooling portion.

10. The headwear according to claim 1, wherein the plurality of secondary cooling portions extend from the first cooling portion at a point which is at most 130 mm from an end of the first cooling portion.

11. The headwear according to claim 1, wherein the plurality of tertiary cooling portions extend from the secondary cooling portions by a distance at least 140 mm.

12. The headwear according to claim 1, further comprising a support structure extending from a neck portion to a front edge portion for covering a wearer's neurocranium, the cooling structure being attached to the support structure.

13. The headwear according to claim 12, wherein the support structure comprises first and second support layers; and the cooling structure is located between these two layers.

14. The headwear according to claim 12, further comprising an attachment portion configured for the user's neck area, wherein the attachment portion comprises a band of pre-stressed material and wherein the band of pre-stressed material is formed as a portion of a ring, extending around at least 2700.

15. The headwear according to claim 12, further comprising an attachment portion configured for the user's neck area, wherein the attachment portion comprises a band of pre-stressed material and wherein the band is arranged to grasp the wearer's neck at the 5th cervical vertebrae or lower.

16. The headwear according to claim 1, wherein the first cooling portion is configured to extend to a location such that when the headwear is worn on a the wearer's head it overlies the confluence of the sinuses.

17. A headwear for cooling a wearer's head, comprising a cooling structure carrying a cooling agent, the cooling structure arranged for cooling the wearer's head and for extending rearwardly past the wearer's internal occipital protuberance when the headwear is worn the wearers head, wherein the cooling structure comprises:
   a first cooling portion arranged to extend over a distance of at least 430mm in a first direction for overlying the superior sagittal sinus when the headwear is worn on the wearer's head, the first cooling portion configured to extend from the 4$^{th}$ cervical vertebrae through the rear of the superior sagittal sinus to the front of the superior sagittal sinus, wherein the first cooling portion has a width of between 50 mm and 60 mm and sets up a temperature gradient between the superior sagittal sinus and the area of the wearer's head adjacent the first cooling portion when the headwear is worn on the wearer's head;

a plurality of secondary cooling portions that extend over a distance of at least 140mm in a second direction from the first cooling portion configured to overlie the transverse sinuses when the headwear is worn on a the wearer's head, wherein the plurality of secondary cooling portions each have a width of between 50 mm and 60 mm and sets up a temperature gradient between the transverse sinuses and an area of the wearer's head adjacent to each secondary cooling portion of the plurality of secondary cooling portions when the headwear is worn on the wearer's head;

a plurality of tertiary cooling portions extending from the secondary cooling portions configured to overlie the sigmoid sinuses and-a the cooling structure of the head, wherein each tertiary cooling portion of the plurality of tertiary cooling portions have a width of between 50 mm and 60 mm to thereby set up a temperature gradient between the sigmoid sinuses and the area of the wearer's head adjacent each tertiary cooling portion of the plurality of tertiary cooling portions when the headwear is worn on the wearer's head; and gaps that do not provide a cooling effect located between the first cooling portions, the plurality of secondary cooling portions and the plurality of tertiary cooling portions.

18. The headwear according to claim 17, wherein the secondary cooling portions extend from the first cooling portion at a point which is from 80 mm to 130 mm from an end of the first cooling portion.

19. The headwear according to claim 17, wherein the first cooling portion is configured to extend to a location such that when the headwear is worn on a the wearer's head it overlies the confluence of the sinuses.

* * * * *